United States Patent
Cole et al.

(10) Patent No.: US 7,544,448 B2
(45) Date of Patent: Jun. 9, 2009

(54) TETRABENZODIAZADIKETOPERYLENE PIGMENTS FOR LASER MARKING

(75) Inventors: Damien Thurber Cole, Drexel Hill, PA (US); Joseph E. Sarver, Erial, NJ (US); Colin Dennis Campbell, Claymont, DE (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 259 days.

(21) Appl. No.: 11/589,530

(22) Filed: Oct. 30, 2006

(65) Prior Publication Data

US 2007/0114494 A1    May 24, 2007

Related U.S. Application Data

(60) Provisional application No. 60/738,455, filed on Nov. 21, 2005.

(51) Int. Cl.
  *G03C 3/00* (2006.01)
  *G03F 7/00* (2006.01)
  *C09K 11/06* (2006.01)
  *C09D 11/00* (2006.01)

(52) U.S. Cl. .................. 430/9; 430/14; 430/270.1; 430/270.15; 430/363; 430/945; 106/31.77; 106/31.15; 252/301.16; 252/301.55; 546/28

(58) Field of Classification Search .................. None
  See application file for complete search history.

(56) References Cited

U.S. PATENT DOCUMENTS

| 4,861,620 | A | | 8/1989 | Azuma et al. | 427/53.1 |
| 5,028,643 | A | * | 7/1991 | Jaffe | 524/90 |
| 6,022,905 | A | | 2/2000 | Harris et al. | 522/2 |
| 6,372,394 | B1 | | 4/2002 | Zientek | 430/10 |
| 2004/0116700 | A1 | * | 6/2004 | Hartmann et al. | 546/13 |
| 2008/0124498 | A1 | * | 5/2008 | Cole et al. | 428/29 |

FOREIGN PATENT DOCUMENTS

| JP | 63-193960 | 8/1988 |
| WO | 02/068431 | 9/2002 |

OTHER PUBLICATIONS

Derwent Abst. No. 1988-267171 [38] of JP 63-193960.
J. Mizuguchi, Dyes and Pigments, vol. 35, No. 4, pp. 347-360 Dec. 1997.
J. Mizuguchi, Molecular Microgiology, Blackwell Scientific, vol. 52, No. Part 9, (Sep. 1996) pp. 2315-2317.

* cited by examiner

*Primary Examiner*—Amanda C. Walke
(74) *Attorney, Agent, or Firm*—Joseph C. Suhadolnik

(57) ABSTRACT

A method for laser marking a substrate which method comprises exposing a composition comprising a tetrabenzodiazadiketoperylene pigment to laser radiation to produce a fluorescent marking readily apparent under UV light is disclosed. Many of the tetrabenzodiazadiketoperylenes herein are novel. This method can yield fluorescent markings which are not readily apparent under ambient light. A method for producing non-fluorescent laser marked substrates containing tetrabenzodiazadiketoperylene dyes is also disclosed.

18 Claims, No Drawings

TETRABENZODIAZADIKETOPERYLENE PIGMENTS FOR LASER MARKING

This application claims benefit under 35 USC 119(e) of U.S. provisional application No. 60/738,455, filed Nov. 21, 2005.

A method for laser marking a substrate which method comprises exposing a composition comprising a tetrabenzodiazadiketoperylene pigment to laser radiation to produce a fluorescent marking readily apparent under UV light is disclosed. This method can yield fluorescent markings which are not readily apparent under ambient light providing a unique opportunity in, for example, security marking and brand identification of printed packaging. Novel tetrabenzodiazadiketoperylene compounds are also disclosed.

Laser marking is a well known and important means for quickly and cleanly inscribing plastic surfaces with identification marks, such as date codes, batch codes, bar codes or part numbers, functional marks, such as computer keyboard characters, and decorative marks, such as company logos. Common laser marks are a dark mark on a lighter colored background or a light mark on a dark colored background. However, colored laser marks on plastic articles, such as electronic components, exterior automotive parts, utensils, and the like, are also desirable in order to eliminate the cost and environmental complications associated with inks, masks, and other printing or hot-stamping methods now used for color imprinting.

The most common mechanism of laser marking of thermoplastic materials depends on the rapid production of heat in the irradiated portion of the plastic due to the absorption of the laser energy. Although some thermoplastics, such as polyethylene, polypropylene and polystyrene, are transparent to laser energy at certain wavelengths, they may be marked by including in the resin composition a laser energy-absorbing additive, such as carbon black, graphite, kaolin, mica, and the like, that increases the rate of temperature rise in the localized portion of the polymer exposed to the laser. Other polymers, such as polyvinylchloride, polyethylene terephthalate and acrylonitrile butadiene styrene (ABS) readily absorb laser energy and require little or no special additives.

A light, dark or colored laser mark on a thermoplastic material may be produced by several different mechanisms or combination of mechanisms, depending on the resin and additives employed, the nature of any colored pigments, and the laser energy characteristics. For example, a dark marking on polyethylene containing an energy absorbing pigment can be produced at a relatively low energy level (3 joules/cm$^2$) by heat-induced carbonization of the polymer and/or the pigment. Polymers that have a low tendency to carbonize, such as polyolefins and high density polyethylene, may show a light mark caused by foaming of the resin due to the heat produced by the laser energy. Other polymers, such as polycarbonate, ABS and polystyrene, tend to carbonize rather than foam. A light or a colored mark on a dark background may also be produced when a dark colored additive, such as carbon black or a dark color pigment, is combined with a resin and exposed to a laser resulting in vaporization or bleaching of the additive to reveal an underlying heat-stable color pigment or dye or natural polymer color. Dark markings can be achieved by using additives that are colorless in the visible light spectrum but which change into a visible dark or black product when irradiated by laser light just outside the visible range.

A light and a dark mark on the same polymer composition has been obtained by first exposing a polyethylene composition containing 1% of a mica-based additive and 0.01% of a red pigment to a laser at a low energy density (<2.5 joules/cm$^2$) to generate a white mark by bleaching the red pigment and the generating a black mark by carbonization of the polyethylene and the additive at a higher energy density (>4 joules/cm$^2$).

U.S. Pat. No. 4,861,620, incorporated herein in its entirety by reference, discloses pigments that undergo a change of internal structure and hence color due to a temperature increase by laser irradiation. Some pigments thermally decompose upon heating at or above the predetermined temperature changing its molecular structure and forming a different color; other pigments undergo a change of crystalline structure which produces a different color. The pigments may be incorporated into a plastic material or may be coated onto the surface of a substrate prior to marking. For Example, the color changing pigment may be incorporated in a lacquer which is applied to the substrate surface.

U.S. Pat. No. 6,022,905, incorporated herein in its entirety by reference, discloses a laser-marked plastic article comprising at least two differently colored laser marks and a method for producing the article by exposing to various laser energies a thermoplastic composition comprising a laser energy absorbing additive and color pigments capable of chemically changing color at higher than a predetermined temperature.

U.S. Pat. No. 6,372,394, incorporated herein in its entirety by reference, relates to a method of marking articles by a laser and more particularly to a method of marking security documents or other documents having a clear substrate covered by opacifying layers.

It has been desirable in the past to produce a laser mark with the highest visual contrast between the mark and the color of the surrounding plastic.

There remains a need, however, for a process for making markings that are not visible under ordinary conditions but become visible when subjected to special conditions, for example, security markings, product codes, part codes and shipping codes which are visible only under ultraviloet (UV) light. These processes are most valuable when readily incorporated into standard manufacturing techniques.

U.S. Pat. No. 5,028,643, incorporated herein in its entirety by reference, discloses tetrabenzodiazadiketoperylene pigments and a method for their preparation.

It has been found that when tetrabenzodiazadiketoperylene pigment compositions, many of which are novel, are exposed to laser marking conditions, markings can be produced that are visible under UV light, but not visible under ambient visible light.

DESCRIPTION OF THE INVENTION

A composition comprising a tetrabenzodiazadiketoperylene pigment (TBDKP) of formula I is provided which composition produces fluorescent markings upon exposure to heat.

One embodiment provides a composition comprising a colorant which colorant is present in a non-fluorescent form and a fluorescent form wherein the non-fluorescent form of the colorant is a tetrabenzodiazadiketoperylene pigment of formula I

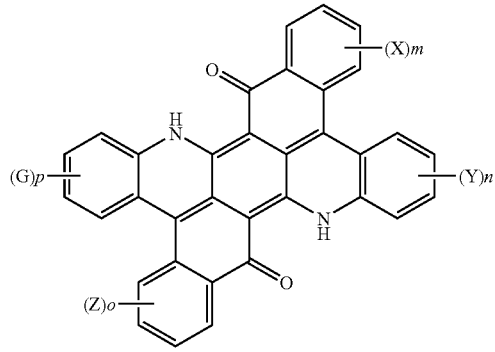

wherein

X, Y, Z and G independently of each other are $C_{1-12}$ alkyl or branched alkyl, $C_{3-6}$ cycloalkyl, $C_{7-12}$ aralkyl, $C_{6-10}$ aryl, $C_{3-9}$ saturated or unsaturated heterocycle, halogen, —OR, $CF_3$, —COOR, —CONR'R, $NO_2$, NR'R, $SO_3H$ or $SO_2NR'R$;

R and R', independently of each other are hydrogen, $C_{1-8}$ alkyl or branched alkyl, $C_{3-6}$ cycloalkyl, $C_{6-10}$ aromatic or $C_{7-12}$ aralkyl;

and m, n, o and p are independently 0, 1, 2, 3 or 4, when m, n, o or p is 2, 3 or 4, each X, Y, Z or G substituent may each be a different group as defined above;

the fluorescent form of the colorant is also of formula I and is obtained from the non-fluorescent pigment form by exposure to heat and wherein the flourescent form of the pigment is present at a higher concentration in defined domains relative to the remainder of the composition to display an identifiable flourescent marking when exposed to ultraviolet light.

Typically the composition also comprises a natural or synthetic polymer, frequently a synthetic polymer. The composition may be in the form of an article, for example a plastic object such as a platelet or sheet, or in the form of a coating.

For example, X, Y, Z and G independently of each other are $C_{1-12}$ alkyl or branched alkyl, $C_{7-12}$ aralkyl, $C_{6-10}$ aryl, F, Cl, Br, I, —OR, —COOR, —CONR'R, $NO_2$, NR'R, $SO_3H$ or $SO_2NR'R$ and m, n, o and p are independently 0, 1, 2, 3 or 4.

For example, X, Y, Z and G independently of each other are $C_{1-12}$ alkyl or branched alkyl, $C_{7-12}$ aralkyl, $C_{6-10}$ aryl, F, Cl, Br, —OR, —COOR, —CONR'R, $NO_2$, NR'R, $SO_3H$ or $SO_2NR'R$ and m, n, o and p are independently 0, 1 or 2.

For example, X, Y, Z and G independently of each other are $C_{1-12}$ alkyl or branched alkyl, F, Cl, —OR, —$NO_2$, NR'R or $SO_3H$ and m, n, o and p are independently 0, 1 or 2.

For example, m, n, o and p are each 0 and the tetrabenzodiazadiketoperylene pigment of formula I is

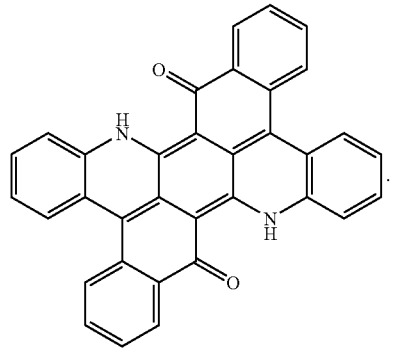

Alkyl or branched alkyl is straight or branched chain of the specified number of carbon atoms and is for example methyl, ethyl, n-propyl, n-butyl, sec-butyl, tert-butyl, n-hexyl, n-octyl, 2-ethylhexyl, n-nonyl, n-decyl, n-undecyl, n-dodecyl.

Fluorescent markings are markings which are luminescent and therefore readily visible, when exposed to ultra-violet light, ultra violet being that part of the electromagnetic spectrum with wavelenths between about 200 and 400 nm.

In one useful aspect of the invention, the composition is a laser markable composition producing defined fluorescent markings upon exposure to the thermal radiation provided by a laser.

Another useful aspect of the invention is that fluorescent markings can be generated that are not readily apparent under ambient light. "Ambient light", "ambient visible light" or "ambient lighting conditions" are the conditions encounterd in normal outdoor or indoor lighting. For example, sunlight or other light which likewise contains large amounts of the part of the electromagnetic spectrum with wavelenths between about 400 and 800 nm, although some ultra violet light with wavelengths below 400 nm may also be present. "Not readily apparent under ambient light" means that there is no visible difference in color under normal outdoor or indoor lighting conditions of the laser marked portion of the substrate and that any visibly discernable change in the appearance of the substrate as a result of laser marking, for example, a change in gloss or color, is absent or perceptible only under rigorous examination or upon exposure to UV light.

For example, the fluorescent markings are the same color as the remainder of the composition under everyday outdoor or indoor lighting.

For example, when a black coating containing a TBDKP is marked with a laser As a source of heat, this can be accomplished using commercially available laser technology, no change is visible under ambient light, i.e. the coating remains black, however, the markings fluoresce a bright red under a black light source (i.e., an ultra violet light source).

For example, the composition displays a uniform color ($\Delta E^* \leq 3$, preferably $\Delta E^* \leq 2$) when viewed under a light source of wavelength in the range from 400 to 700 nm, such as ambient visible light, or when measured with a CIE L*A*B* color measuring equipment under exclusion of UV light.

The TBDKP pigment is present in the laser markable composition in an "effective amount", that is an amount that provides both the desired level of pigmentation for the substrate or coating and an amount that lends itself to laser marking using acceptable irradiation conditions. For example, the TBDKP pigment is present in an amount of as little as 0.01 to 15% weight percent based on the total weight of the composition, for example 0.1 to 10% based on the total weight of the composition, but can be present in much higher amounts, for example as high as 50% to 99% especially when used in a coating or impregnated into the surface of an article.

Accordingly, the amount of polymer in a composition may be from 1 to 99.999% by weight, based on the total weight of the composition. The composition may also comprise further components, such as described below, in amounts, for example, from 0.001 to 90% by weight of further components, based on the total weight of the composition.

The laser markable composition may be a synthetic or naturally occuring polymeric substrate, for example a film forming polymer, comprising a tetrabenzodiazadiketoperylene pigment of formula I.

Another aspect of the present invention is to provide a laser markable composition which is a coating comprising a tetrabenzodiazadiketoperylene pigment of formula I which can be applied to the surface a substrate which can then be laser marked. The coating can comprise any coating system, or even be a preformed film, which both adheres to the substrate and is compatible with the tetrabenzodiazadiketoperylene pigments. A coating or film in which the TBDKP pigment is overly soluble will cause the system to fluoresce without heat exposure and is not appropriate for this aspect of the invention.

Typically, the coating comprises a polymeric binder which can in principle be any binder customary in industry, for example those described in Ullmann's Encyclopedia of Industrial Chemistry, 5th Edition, Vol. A18, pp. 368-426, VCH, Weinheim 1991. In general, it is a film-forming binder based on a thermoplastic or thermosetting resin, predominantly on a thermosetting resin. Examples thereof are alkyd, acrylic, acrylamide, polyester, styrenic, phenolic, melamine, epoxy and polyurethane resins.

For example, non-limiting examples of common coating binders useful in the present invention include silicon containing polymers, fluorinated polymers, unsaturated polyesters, unsaturated polyamides, polyimides, crosslinkable acrylic resins derived from substituted acrylic esters, e.g. from epoxy acrylates, urethane acrylates, polyester acrylates, polymers of vinyl acetate, vinyl alcohol and vinyl amine. The coating binder polymers may be co-polymers, polymer blends or composites.

Coatings are frequently crosslinked with, for example, melamine resins, urea resins, isocyanates, isocyanurates, polyisocyanates, epoxy resins, anhydrides, poly acids and amines, with or without accelerators.

The binder can be a cold-curable or hot-curable binder provided that the temperature is not high enough to cause dissolution of the tetrabenzodiazadiketoperylene pigment; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

The binder may be a surface coating resin which dries in the air or hardens at room temperature. Exemplary of such binders are nitrocellulose, polyvinyl acetate, polyvinyl chloride, unsaturated polyester resins, polyacrylates, polyurethanes, epoxy resins, phenolic resins, and especially alkyd resins. The binder may also be a mixture of different surface coating resins. Provided the binders are curable binders, they are normally used together with a hardener and/or accelerator.

Examples of Coating Compositions Containing Specific Binders are:
1. coatings based on cold- or hot-crosslinkable alkyd, acrylate, polyester, epoxy or melamine resins or mixtures of such resins, if desired with addition of a curing catalyst;
2. two-component polyurethane coatings based on hydroxyl-containing acrylate, polyester or polyether resins and aliphatic or aromatic isocyanates, isocyanurates or polyisocyanates;
3. one-component polyurethane coatings based on blocked isocyanates, isocyanurates or polyisocyanates which are deblocked during baking, if desired with addition of a melamine resin;
4. one-component polyurethane coatings based on a Tris-alkoxycarbonyltriazine crosslinker and a hydroxyl group containing resin such as acrylate, polyester or polyether resins;
5. one-component polyurethane coatings based on aliphatic or aromatic urethaneacrylates or polyurethaneacrylates having free amino groups within the urethane structure and melamine resins or polyether resins, if necessary with curing catalyst;
6. two-component coatings based on (poly)ketimines and aliphatic or aromatic isocyanates, isocyanurates or polyisocyanates;
7. two-component coatings based on (poly)ketimines and an unsaturated acrylate resin or a polyacetoacetate resin or a methacrylamidoglycolate methyl ester;
8. two-component coatings based on carboxyl- or amino-containing polyacrylates and polyepoxides;
9. two-component coatings based on acrylate resins containing anhydride groups and on a polyhydroxy or polyamino component;
10. two-component coatings based on acrylate-containing anhydrides and polyepoxides;
11. two-component coatings based on (poly)oxazolines and acrylate resins containing anhydride groups, or unsaturated acrylate resins, or aliphatic or aromatic isocyanates, isocyanurates or polyisocyanates;
12. two-component coatings based on unsaturated polyacrylates and polymalonates;
13. thermoplastic polyacrylate coatings based on thermoplastic acrylate resins or externally crosslinking acrylate resins in combination with etherified melamine resins;
14. paint systems based on siloxane-modified or fluorine-modified acrylate resins.

Acrylic, methacrylic and acrylamide polymers and co-polymers dispersible in water are readily used as a binder in the present invention. For example, acrylic, methacrylic and acrylamide dispersion polymers and co-polymers.

For example, coatings or films comprising acrylate polymers are useful in the fluorescent marking compositions of the instant invention.

The coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429-471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzyl-ammonium chloride.

Amino-containing resins are simultaneously binder and curing catalyst. Examples thereof are amino-containing acrylate copolymers.

The curing catalyst used can also be a phosphine, for example triphenylphosphine.

The coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the abovementioned publication Ullmann's Encyclopedia of Industrial Chemistry, 5th Edition, Vol. A18, pages 451-453. In radiation-curable coating compositions, the novel stabilizers can also be employed without the addition of sterically hindered amines.

The coating may also be a radiation-curable, solvent-free formulation of photopolymerisable compounds. Illustrative examples are mixtures of acrylates or methacrylates, unsaturated polyester/styrene mixtures or mixtures of other ethylenically unsaturated monomers or oligomers.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438-444. The powder coating material may also have the form of a powder-slurry (dispersion of the powder preferably in water).

Multilayer systems are possible here as well, where the tetrabenzodiazadiketoperylene pigment may reside in a coating which is then itself coated with another coating, such as a protective coating.

When used in a coating, the compounds of formula I are incorporated into the coating via techniques common in the art.

Typically a coating comprises 0.01-50% by weight of tetrabenzodiazadiketoperylene pigment based on the total weight of the solid binder, for example, 0.01-15%, or 0.1-10% or 0.1-5% by weight based on the total weight of the solid binder.

The coating composition according to the invention can be applied to any desired substrate, for example to metal, wood, plastic, composite, glass or ceramic material substrates by the customary methods, for example by brushing, spraying, pouring, draw down, spin coating, dipping or electrophoresis; see also Ullmann's Encyclopedia of Industrial Chemistry, 5th Edition, Vol. A18, pp. 491-500.

This invention also provides a method for laser marking a substrate which method comprises exposing a composition containing the TBDKP pigments of formula I to laser irradiation to produce a defined marking that fluoresces under exposure to UV light. The TBDKP pigments may be incorporated directly into an article, such as a plastic article, or the pigments may be applied as a coating or film on the surface of a substrate.

That is a method for laser marking a substrate which method comprises incorporating into or applying onto the substrate a composition according to claim 1 comprising a tetrabenzodiazadiketoperylene pigment, and then exposing the substrate to laser radiation to produce a fluorescent marking.

That is a method for laser marking a substrate which method comprises incorporating into or applying onto the substrate a composition comprising a tetrabenzodiazadiketoperylene pigment, and then exposing one or more (for example 1 to $10^6$) parts of the substrate to laser radiation or to heat to produce a fluorescent marking. Methods of creating pattern by using a laser or a heat source are per se well-known in the art.

The laser used to mark the substrate may be any laser that delivers radiation at wavelengths that are absorbed by the laser marking composition in a manner which discreetly heats the portion of the substrate to leave the desired marking. The marking can be any marking including letters, numbers, bar codes, geometric shapes and other figures including logos and other designs.

For Example, lasers used to produce markings visible under ambient lighting are useful in the present invention. For Example, color marks have been formed on a dark background by a Nd:YAG laser or a frequency doubled Nd:YAG laser (wavelength 532 nm), employing a polyacetal copolymer resin or a polybutylene terephthalate resin combined with a mineral black pigment (bone charcoal, bone black or ivory black) that is removed or destroyed by the laser, and a heat-stable organic and/or inorganic pigment or a polymer-soluble dye. Color marks have also been achieved with a Nd:YAG laser on thermoplastics that have been colored by an organic dye or pigment and an inorganic pigment of the same color, and which also contain carbon black. These color marks have the same color as the background color of the plastic, but have a lighter tone.

Such lasers and other lasers useful in the invention are known and many are commercialy available.

Methods for deflecting the laser beam through a mask or otherwise directed over the surface of the object to be marked, in conformity with the shape of the marking which is to be applied are likewise known.

The instant invention further provides a laser marked substrate comprising the TBDKP pigments of formula I. The laser marked substrate may have the TBDKP pigments incorporated therein or the TBDKP pigments may be incorporated in a coating or film which is applied to the surface of the substrate.

When the pigments of the instant invention are used in a preformed film, the film is comprised of one or more polymers corrresponding to the binder resins above. The film can be prepared by casting from a solution or other method and can be conviently applied to the surface of the substrate by, for example, the use of an adhesive.

The coating or film comprising the present TBDKP pigments may also optionally have incorporated therein other additives such as antioxidants, UV absorbers, hindered amine or other light stabilizers, phosphites or phosphonites, benzofuran-2-ones, thiosynergists, polyamide stabilizers, metal stearates, nucleating agents, fillers, reinforcing agents, lubricants, emulsifiers, dyes, pigments, dispersents, optical brighteners, flame retardants, antistatic agents, blowing agents and the like, or mixtures thereof.

More than one TBDKP pigment can be used in any composition or method herein.

Other types of pigments and colorants such as dyes may also be present.

When the present TBDKP pigments are incorporated into a substrate or coating into which the TBDKP pigments dissolve, TBDKP dyes result. TBDKP dyes also result when the composition comprising them is heated to a sufficiently high temperature. The TBDKP dyes will themselves fluoresce making the production of visually fluorescent laser markings problematic.

However, the compositions comprising TBDKP dyes can still be useful in laser marking processes. For example, if a TBDKB dye is present throughout certain compositions, exposure of those compositions to laser radiation as described above, with the same or similar laser sources, will cause destruction of the dye generating markings that will appear visibly less colored, i.e., lighter, under normal indoor or outdoor conditions, or markings that are visible under ultra violet light because they do not fluoresce while the non-marked area with the intact dye does fluoresce.

Methods for producing laser marks by dye bleaching of dye compositions are known in the art as described above and are readily modified to suit the present needs. See also the discussion in U.S. Pat. No. 6,022,905. Other pigments, dye and colorants may also be present. The composition may also include a laser energy-absorbing additive, such as carbon black, graphite, kaolin, mica, and the like, that increases the rate of temperature rise in the localized portion of the polymer exposed to the laser. Laser energy absorbing additives are also known to causing dye bleaching or other dye transformation by energy transfer mechanisms to the dye directly.

In one embodiment of the present invention laser energy absorbing additives are present in the markable composition; in another embodiment of the invention laser energy absorbing additives are not present in the markable composition.

The substrate in which TBDKP dyes are incorporated may be, for example, a naturally occuring polymer or a synthetic polymer.

The naturally occuring or synthetic polymer containing the TBDKP dyes may be, for example, a thermoplastic, thermost, crosslinked or inherently crosslinked polymer, for example, a polyolefin, polyamide, polyurethane, polyacrylate, polyacrylamide, polyvinyl alcohol, polycarbonate, polystyrene, polyester, polyacetal, a natural or synthetic rubber or a halogenated vinyl polymer such as PVC. The polymer may be a co-polymer, a polymer blend or part of a composite.

The polymer may be, for example, in the form of a film, sheet, injection-moulded article, extruded workpiece, fiber, laiminate, felt or woven fabric. The polymer may also be part of a coating composition.

The TBDKP dyes, or the TBDKP pigments which convert to dyes may be incorporated into polymer resins according a variety of known methods. For example, the compounds may be added as an individual component during blending, for example, dry blending of the resin prior to prior to processing, or the compound may be added as a blend, master batch, flush, or other concentrate in another substance prior to processing. The compounds may also be added during processing steps. Standard process steps for polymer resins are well known in the literature and include extrusion, coextrusion, compression molding, Brabender melt processing, film formation, injection molding, blow molding, other molding and sheet forming processes, fiber formation, surface impregnation, suspension, dispersion etc.

The TBDKP dye containing polymer composition may also optionally have incorporated therein other additives such as antioxidants, UV absorbers, hindered amine or other light stabilizers, phosphites or phosphonites, benzofuran-2-ones, thiosynergists, polyamide stabilizers, metal stearates, nucleating agents, fillers, reinforcing agents, lubricants, emulsifiers, dyes, pigments, dispersents, optical brighteners, flame retardants, antistatic agents, blowing agents and the like, or mixtures thereof.

Many tetrabenzodiazadiketoperylene colorants of formula I are novel. Particular embodiments of the present invention therefore relate to tetrabenzodiazadiketoperylene compounds of formula I above which necessarily bear at least one non-hydrogen substituent on a carbon atom of the benzo rings.

That is, a compound of formula I, wherein m is m is 1, 2, 3 or 4 and n, o and p are independently 0, 1, 2, 3 or 4.

For example, a compound of formula I, wherein X, Y, Z and G independently of each other are $C_{1-12}$ alkyl or branched alkyl, $C_{7-12}$ aralkyl, $C_{6-10}$ aryl, F, Cl, Br, —OR, —COOR, —CONR'R, $NO_2$, NR'R, $SO_3H$ or $SO_2NR'R$; m is 1 or 2 and n, o and p are independently 0, 1 or 2.

For example, a compound of formula I, wherein X, Y, Z and G independently of each other are $C_{1-12}$ alkyl or branched alkyl, F, Cl, —OR, —$NO_2$, NR'R or $SO_3H$.

Other embodiments relate to compositions comprising a natural or synthetic polymer and a novel compound of formula I, wherein m is m is 1, 2, 3 or 4 and n, o and p are independently 0, 1, 2, 3 or 4. For example the natural or synthetic polymer is a polymer described above, for example, a thermoplastic, thermost, crosslinked or inherently crosslinked polymer, for example, a polyolefin, polyamide, polyurethane, polyacrylate, polyacrylamide, polyvinyl alcohol, polycarbonate, polystyrene, polyester, polyacetal, a natural or synthetic rubber or a halogenated vinyl polymer such as PVC. The polymer may be a co-polymer, a polymer blend or part of a composite.

EXAMPLES

Example 1

A mixture of 2.3 grams of toner of black etrabenzodiazadiketoperylene pigment (dibenz[3,4:5,6]isoquino[1,8-bc]naphth[1,2,3-mn]acridine-10,20-dione, 9,19-dihydro-),
1.2 grams of DISPERBYK 161, 16.9 grams of an acrylic mill base and 39.3 grams of a letdown is milled with 100 grams of 2 mm glass beads using a SKANDEX mill. The resulting paint is separated from the beads.

A drawdown of the paint using a 100 micron wet film wired bar and a KCC automatic film applicator is prepared and dried over a white/black leneta card. The black coating over the white part of the card is laser marked. The black coating appears unchanged under ambient visible light, but under black light (UV light) the mark fluoresces bright red.

Example 2

The proceedure of Example 1 is repeated using a toner prepared with the brown 6,16-di-chloro tetrabenzodiazadiketoperylene pigment to provide a brown coating which is laser marked. The brown coating appears unchanged under ambient visible light, but under black light (UV light) the mark fluoresces bright red.

Example 3

A mixture of 10 g of toner of the black tetrabenzodiazadiketoperylene, 100 g POLANE G, (Polyurethane coating from The SHERWIN-WILLIAMS COMPANY) and 100 g of 2 mm glass beads is shaken for 2 hours using a SKANDEX mill. The resulting millbase is separated from the beads.

To the resulting millbase is added one third by weight of catalyst isocyanate followed by mixing. This paint is drawdown with a 3 mil bar over a white/black leneta card. The coating is allowed to cure at room temperature overnight. Then the black coating over the white part of the card is laser marked. The black coating appears unchanged under ambient visible light, but under black light (UV light) the mark fluoresces red.

What is claimed is:

1. A method for marking a substrate which method comprises incorporating into or applying onto the substrate a composition comprising a tetrabenzodiazadiketoperylene pigment of formula I

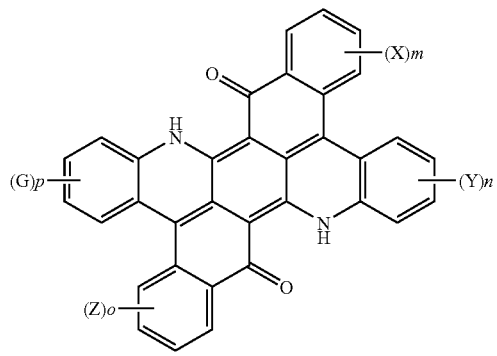

wherein
X, Y, Z and G independently of each other are
$C_{1-12}$ alkyl or branched alkyl, $C_{3-6}$ cycloalkyl, $C_{7-12}$ aralkyl, $C_{6-10}$ aryl, $C_{3-9}$ saturated or unsaturated heterocycle, halogen, —OR, $CF_3$, —COOR, —CONR'R, $NO_2$, NR'R, $SO_3H$ or $SO_2NR'R$;
R and R', independently of each other are hydrogen, $C_{1-8}$ alkyl or branched alkyl, $C_{3-6}$ cycloalkyl, $C_{6-10}$ aromatic or $C_{7-12}$ aralkyl;
and m, n, o and p are independently 0, 1, 2, 3 or 4, when m, n, o or p is 2, 3 or 4, each X, Y, Z or G substituent may each be a different group as defined above,
and then exposing one or more parts of the substrate to laser radiation or heat to obtain a fluorescent form of the pigment of formula I to produce a fluorescent marking.

2. A method according to claim 1, which produces on a substrate a fluorescent marking that is not discernable under ambient visible light.

3. A method according to claim 1, which produces on a substrate a fluorescent marking which remains the same color when viewed under ambient visible light as the portion of the substrate which is not so marked.

4. A method according to claim 1, wherein the composition comprising a tetrabenzodiazadiketoperylene pigment is a coating applied to the surface of a substrate.

5. A method according to claim 4, wherein the coating comprises an acrylate polymer.

6. A method for marking a substrate according to claim 1, wherein the fluorescent marking is produced upon exposing one or more parts of the substrate to laser radiation.

7. A laser marked substrate containing flourescent markings resulting from exposure to laser radiation, comprising a substrate which has incorporated therein or applied thereto a composition
comprising a colorant, which colorant is present in a non-fluorescent form and a fluorescent form, wherein the non-fluorescent form of the colorant is a tetrabenzodiazadiketoperylene pigment of formula I

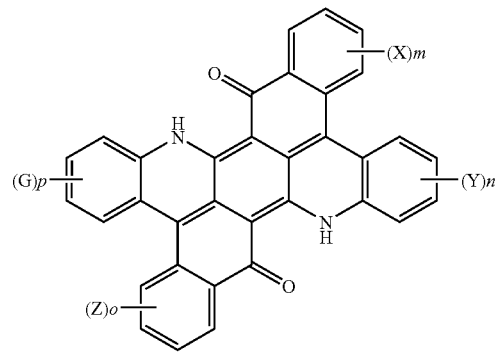

wherein
X, Y, Z and G independently of each other are
$C_{1-12}$ alkyl or branched alkyl, $C_{3-6}$ cycloalkyl, $C_{7-12}$ aralkyl, $C_{6-10}$ aryl, $C_{3-9}$ saturated or unsaturated heterocycle, halogen, —OR, $CF_3$, —COOR, —CONR'R, $NO_2$, NR'R, $SO_3H$ or $SO_2NR'R$;
R and R', independently of each other are hydrogen, $C_{1-8}$ alkyl or branched alkyl, $C_{3-6}$ cycloalkyl, $C_{6-10}$ aromatic or $C_{7-12}$ aralkyl;
and m, n, o and p are independently 0, 1, 2, 3 or 4, when m, n, o or p is 2, 3 or 4, each X, Y, Z or G substituent may each be a different group as defined above;
wherein the fluorescent form of the colorant is also of formula I and is obtained from the non-fluorescent pigment form by exposure to heat from laser radiation and wherein the flourescent form of the pigment is present at a higher concentration in defined domains relative to the remainder of the composition to display an identifiable flourescent marking when exposed to ultraviolet light.

8. A laser marked substrate according to claim 7, wherein the composition comprising a tetrabenzodiazadiketoperylene pigment is a polymeric film or coating applied to the surface of the substrate.

9. A laser marked substrate according to claim 7, wherein the defined florescent markings are the same color when viewed under ambient visible light as the portion of the substrate which does not contain fluorescent laser markings.

10. A laser marked substrate according to claim 8, wherein the polymer composition comprising a tetrabenzodiazadiketoperylene pigment is a coating.

11. A laser marked substrate according to claim 8, wherein the polymer composition comprising a tetrabenzodiazadiketoperylene pigment is a polymeric film.

12. A method for marking a substrate which method comprises incorporating into or applying onto substrate a composition comprising a natural or synthetic polymer and an effective amount of a fluorescent dye of formula I which composition produces a non-fluorescent marking upon exposure to heat

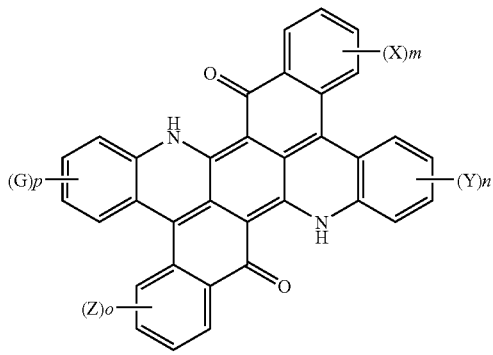

I wherein
X, Y, Z and G independently of each other are
$C_{1-12}$ alkyl or branched alkyl, $C_{3-6}$ cycloalkyl, $C_{7-12}$ aralkyl, $C_{6-10}$ aryl, $C_{3-9}$ saturated or unsaturated heterocycle, halogen, —OR, $CF_3$, —COOR, —CONR'R, $NO_2$, NR'R, $SO_3H$ or $SO_2NR'R$;
R and R', independently of each other are hydrogen, $C_{1-8}$ alkyl or branched alkyl, $C_{3-6}$ cycloalkyl, $C_{6-10}$ aromatic or $C_{7-12}$ aralkyl;
and m, n, o and p are independently 0, 1, 2, 3 or 4, when m, n, o or p is 2, 3 or 4, each X, Y, Z or G substituent may each be a different group as defined above, and then exposing one or more parts of the substrate to laser radiation or heat.

13. A laser marked substrate obtained by the method according to claim 12.

14. A method according to claim 1, wherein the composition comprising a tetrabenzodiazadiketoperylene pigment of formula I comprises a natural or synthetic polymer.

15. A method according to claim 14, wherein the composition comprising a tetrabenzodiazadiketoperylene pigment of formula I comprises a synthetic polymer.

16. A laser marked substrate acording to claim 7, wherein the composition comprising a colorant which is present in a non-fluorescent form and a fluorescent form, wherein the non-fluorescent form of the colorant is a tetrabenzodiazadiketoperylene pigment of formula I comprises a natural or synthetic polymer.

17. A laser marked substrate acording to claim 16, wherein the composition comprising a tetrabenzodiazadiketoperylene pigment of formula I is a synthetic polymer.

18. A method according to claim 12, wherein the composition comprising an effective amount of a fluorescent dye of formula I comprises a synthetic polymer.

* * * * *